United States Patent
Nakamura et al.

(10) Patent No.: US 9,351,915 B2
(45) Date of Patent: May 31, 2016

(54) ASCORBIC ACID DERIVATIVE COMPOSITION AND PRODUCTION METHOD OF THE SAME, ASCORBIC ACID DERIVATIVE SOLUTION, AND SKIN EXTERNAL PREPARATION

(71) Applicant: SHOWA DENKO K.K., Minato-ku, Tokyo (JP)

(72) Inventors: Keiichi Nakamura, Kawasaki (JP); Takanori Aoki, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 14/378,504

(22) PCT Filed: Oct. 11, 2013

(86) PCT No.: PCT/JP2013/077784
§ 371 (c)(1),
(2) Date: Aug. 13, 2014

(87) PCT Pub. No.: WO2014/097721
PCT Pub. Date: Jun. 26, 2014

(65) Prior Publication Data
US 2015/0031650 A1    Jan. 29, 2015

(30) Foreign Application Priority Data

Dec. 20, 2012   (JP) ................................ 2012-278725

(51) Int. Cl.
| C07D 407/00 | (2006.01) |
| A61K 8/67 | (2006.01) |
| A61Q 19/00 | (2006.01) |
| C07F 9/655 | (2006.01) |
| A61K 8/55 | (2006.01) |

(52) U.S. Cl.
CPC . *A61K 8/676* (2013.01); *A61K 8/55* (2013.01); *A61Q 19/00* (2013.01); *C07F 9/65515* (2013.01); *A61K 2800/5922* (2013.01)

(58) Field of Classification Search
CPC .... C07D 309/38; C07D 307/62; A61K 8/676; A61K 8/55; A61K 2800/5922; A61Q 19/00; C07F 9/65515
USPC .................................................. 549/295, 273
See application file for complete search history.

(56) References Cited

U.S. PATENT DOCUMENTS

| 6,127,409 A | * | 10/2000 | Suzuki ................... A61K 8/676 514/473 |
| 8,853,172 B2 | * | 10/2014 | Masuta et al. .................. 514/25 |
| 2007/0141000 A1 | | 6/2007 | Nishimura et al. |

FOREIGN PATENT DOCUMENTS

| JP | 43-9218 S | 4/1968 |
| JP | 61-152613 A | 7/1986 |
| JP | 10-298174 A | 11/1998 |
| JP | 2000-226578 A | 8/2000 |
| JP | 2000226578 | * 8/2000 |
| JP | 2007-56009 A | 3/2007 |
| JP | 2012-236800 A | 12/2012 |
| WO | 2011/030816 A1 | 3/2011 |
| WO | 2012153825 A2 | 11/2012 |

OTHER PUBLICATIONS

International Search Report for PCT/JP2013/077784 dated Dec. 17, 2013 [PCT/ISA/210].
Communication dated Jul. 10, 2015 from the European Patent Office in counterpart application No. 13866411.5.

* cited by examiner

*Primary Examiner* — T. Victor Oh
(74) *Attorney, Agent, or Firm* — Sughrue Mion, PLLC

(57) ABSTRACT

An ascorbic acid derivative composition of a first aspect according to the present invention consists of a salt of a compound (1) represented by a general formula (1) shown below; and a salt of a compound (2) represented by a general formula (2) shown below, wherein a ratio of the salt of the compound (2) with respect to a total amount of the salt of the compound (1) and the salt of the compound (2) is from 0.1 to 10% by mass,

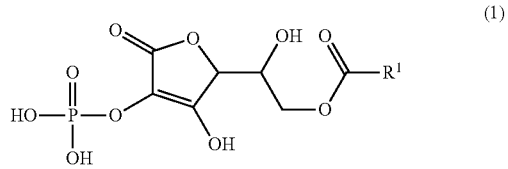

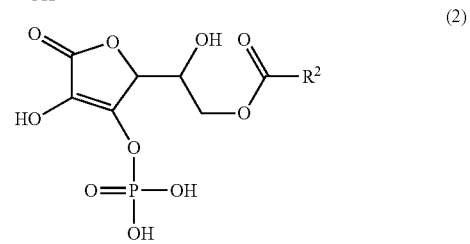

wherein $R^1$ represents a linear or branched alkyl group of 6 to 20 carbon atoms, $R^2$ represents a linear or branched alkyl group of 6 to 20 carbon atoms, and $R^1$ and $R^2$ are the same or are different from each other.

16 Claims, No Drawings

ASCORBIC ACID DERIVATIVE COMPOSITION AND PRODUCTION METHOD OF THE SAME, ASCORBIC ACID DERIVATIVE SOLUTION, AND SKIN EXTERNAL PREPARATION

CROSS-REFERENCE TO RELATED APPLICATIONS

This application is a National Stage of International Application No. PCT/JP2013/077784 filed on Oct. 11, 2013, which claims priority from Japanese Patent Application No. 2012-278725 filed on Dec. 20, 2012, the contents of which are incorporated herein by reference.

TECHNICAL FIELD

The present invention relates to an ascorbic acid derivative composition and a production method of the same, an ascorbic acid derivative solution, and a skin external preparation.

Priority is claimed on Japanese Patent Application No. 2012-278725, filed Dec. 20, 2012, the content of which is incorporated herein by reference.

BACKGROUND ART

Ascorbic acid (vitamin C) has functions such as inhibition of lipid peroxide production, inhibition of collagen formation, retardation of melanin formation and enhancement of immune functions, and has heretofore been used in the fields of medicines, agricultural chemicals, animal drugs, foods, feeds, cosmetics, and the like for these purposes.

However, since ascorbic acid is poor in stability and has also poor lipid solubility, the amount thereof which permeates through the cell membrane and accumulates in the cells is also limited. For this reason, there is a trend in that by the use of ascorbic acid itself, the physiological actions of vitamin C cannot necessarily be achieved to a sufficient degree.

In order to improve the stability and lipid solubility of ascorbic acid, various ascorbic acid derivatives have been proposed. It has been thought that among the ascorbic acid derivatives, the ascorbic acid-2-phosphoric acid derivatives in which the hydroxyl group at the 2-position of ascorbic acid is esterified with a phosphoric acid are difficult to oxidize in air, and thus exhibit excellent stability. In addition, it has been considered that the derivatives in which the hydroxyl group of ascorbic acid is acylated with a higher fatty acid is excellent in lipid solubility.

In Patent Document 1, a method of producing a 6-O-higher acylascorbic acid-2-phosphoric acid ester and results of the structure determination of the substance have been described. It has been described that the 6-O-higher acylascorbic acid-2-phosphoric acid ester produced by this method is improved both in stability and in lipid solubility, and is easily taken up into cells. The 6-O-higher acylascorbic acid-2-phosphoric acid esters are usually used in the form of salts.

An emulsified skin external preparation containing 0.03 to 25% by mass of a salt of a 6-O-higher acylascorbic acid-2-phosphoric acid ester and 0.05 to 25% by mass of a glycerin monofatty acid ester has been disclosed in Patent Document 2. It has been described that in the emulsified skin external preparation, the decrease of the salt of 6-O-higher acylascorbic acid-2-phosphoric acid ester due to decomposition can be suppressed by the coexistence of the glycerin monofatty acid ester.

CITATION LIST

Patent Documents

Patent Document 1: Japanese Unexamined Patent Application, First Publication No. Hei 10-298174

Patent Document 2: Japanese Unexamined Patent Application, First Publication No. 2007-56009

DISCLOSURE OF INVENTION

Problem to be Solved by the Invention

However, the stability of the salts of 6-O-higher acylascorbic acid-2-phosphoric acid esters and particularly the sodium salt of 6-O-palmitoyl ascorbic acid-2-phosphoric acid ester is not sufficient yet.

In addition, when using the salts of 6-O-higher acylascorbic acid-2-phosphoric acid esters for the applications listed above, especially in skin external preparations, such as cosmetics, it is common to prepare a formulation by dissolving in an aqueous medium (for example, water or water containing an alcohol), although the salts of 6-O-higher acylascorbic acid-2-phosphoric acid esters exhibit poor solubility therein, which is also a problem.

The present invention is made in view of the above circumstances, and has an object of providing an ascorbic acid derivative composition exhibiting excellent stability and also exhibiting excellent solubility in an aqueous medium, and a production method thereof, an ascorbic acid derivative solution containing the ascorbic acid derivative composition, and a skin external preparation.

Solution to Problem

As a result of extensive studies to solve the above problems, the inventors of the present invention found that the above problems can be solved by allowing a salt of 6-O-higher acylascorbic acid-2-phosphoric acid ester to coexist with a small amount of a salt of 6-O-higher acylascorbic acid-3-phosphoric acid ester, thereby leading to completion of the present invention.

The present invention includes the following aspects.

[1] An ascorbic acid derivative composition consisting of: a salt of a compound (1) represented by a general formula (1) shown below; and a salt of a compound (2) represented by a general formula (2) shown below, wherein a ratio of the salt of the compound (2) with respect to a total amount of the salt of the compound (1) and the salt of the compound (2) is from 0.1 to 10% by mass.

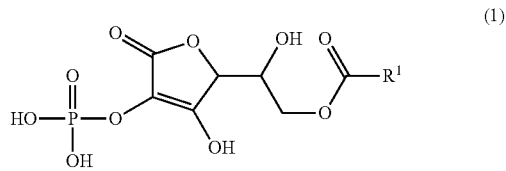
(1)

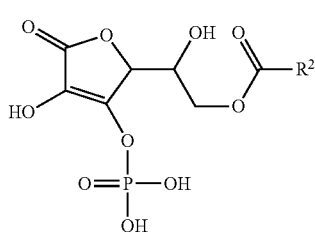

(In the formula, $R^1$ represents a linear or branched alkyl group of 6 to 20 carbon atoms, $R^2$ represents a linear or branched alkyl group of 6 to 20 carbon atoms, and $R^1$ and $R^2$ are the same or are different from each other.)

[2] The ascorbic acid derivative composition according to [1], wherein $R^1$ in the general formula (1) and $R^2$ in the general formula (2) are the same.

[3] The ascorbic acid derivative composition according to [1] or [2], wherein each of $R^1$ in the general formula (1) and $R^2$ in the general formula (2) is a linear alkyl group of 15 carbon atoms.

[4] The ascorbic acid derivative composition according to any one of [1] to [3], wherein each of the salt of the compound (1) and the salt of the compound (2) is a salt of at least one type of metal selected from the group consisting of an alkali metal and an alkaline earth metal.

[5] The ascorbic acid derivative composition according to any one of [1] to [4], wherein each of the salt of the compound (1) and the salt of the compound (2) is a salt of at least one type of metal selected from the group consisting of sodium, potassium, magnesium, and calcium.

[6] An ascorbic acid derivative solution, which is obtained by dissolving the ascorbic acid derivative composition described in any one of [1] to [5] in at least one type of aqueous medium selected from the group consisting of water and an alcohol.

[7] A skin external preparation, which comprises the ascorbic acid derivative composition described in any one of [1] to [5], or the ascorbic acid derivative solution according to [6].

[8] The cosmetic according to [7], wherein the skin external preparation is a cosmetic.

[9] A production method of the ascorbic acid derivative composition described in any one of [1] to [5], wherein the method comprises a step of mixing the salt of the compound (1) and the salt of the compound (2).

[10] A production method of the ascorbic acid derivative composition described in any one of [1] to [5], wherein the method comprises:
a step of obtaining a mixture of the compound (1) and the compound (2) by isomerizing a portion of the compound (1) under an acidic condition; and
a step of neutralizing the mixture.

[11] The production method according to [10], wherein the acidic condition is a pH of 1 to 6.

Effects of Invention

According to the present invention, it is possible to provide an ascorbic acid derivative composition exhibiting excellent stability and also exhibiting excellent solubility in an aqueous medium, and a production method thereof, an ascorbic acid derivative solution containing the ascorbic acid derivative composition, and a skin external preparation.

BEST MODE FOR CARRYING OUT THE INVENTION

A more detailed description of the present invention is presented below. An ascorbic acid derivative composition of the present invention consists of a salt of a compound (1) represented by a general formula (1) shown below; and a salt of a compound (2) represented by a general formula (2) shown below, wherein a ratio of the salt of the compound (2) with respect to a total amount of the salt of the compound (1) and the salt of the compound (2) is from 0.1 to 10% by mass.

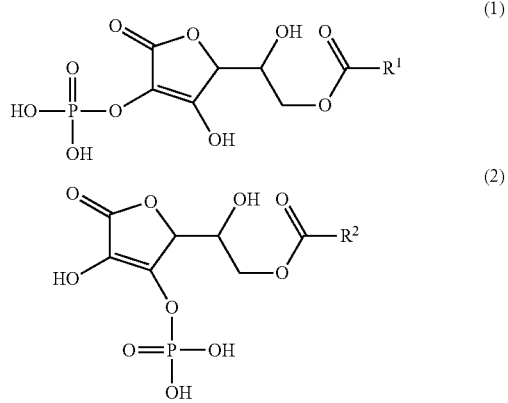

(In the formula, $R^1$ represents a linear or branched alkyl group of 6 to 20 carbon atoms, $R^2$ represents a linear or branched alkyl group of 6 to 20 carbon atoms, and $R^1$ and $R^2$ are the same or are different from each other.)

The compound (1) is a so-called 6-O-higher acylascorbic acid-2-phosphoric acid ester (also referred to as an ascorbic acid-2-phosphoric acid-6-higher fatty acid).

In the general formula (1), $R^1$ is a linear or branched alkyl group having 6 to 20 carbon atoms.

$R^1$ is preferably a linear or branched alkyl group of 10 to 18 carbon atoms, more preferably a linear or branched alkyl group of 12 to 16 carbon atoms, and particularly preferably a linear alkyl group of 15 carbon atoms from the viewpoint of raw material availability, or the like. That is, as the compound (1), a 6-O-palmitoyl ascorbic acid-2-phosphoric acid ester (also referred to as an ascorbic acid-2-phosphoric acid-6-palmitate) is particularly preferred.

The salt of the compound (1) is one obtained by neutralizing the compound (1) with a base, and is a compound formed from an anion derived from the compound (1) and a counter ion (cation derived from the base).

The anion derived from the compound (1) is usually a monovalent to tetravalent anion in which a hydrogen atom is dissociated from at least one of four hydroxyl groups in the compound (1) (two hydroxyl groups bonded to the phosphorus atom and the hydroxyl groups bonded to the carbon atoms at the 3-position and 5-position on the ascorbic acid, respectively).

The counter ion forming a salt with the anion is not particularly limited as long as it does not substantially inhibit the use of ascorbic acid derivatives, and examples thereof include alkali metal ions such as sodium and potassium, alkaline earth metal ions such as magnesium, calcium, and barium, ammonium ions, alkanolamine ions, alkylamine ions, and amino acids. Because of easy availability of the salt of the compound (1) and the raw material thereof, easy incorporation of the ascorbic acid derivative compositions into a formulation containing an aqueous medium, or the like, as the counter ion, at least one type of metal ion selected from the group consisting of alkali metal ions and alkaline earth metal ions is preferred. That is, the salt of the compound (1) is preferably a salt of at least one type of metal selected from the group consisting of alkali metals and alkaline earth metals. As the aforementioned metal, since the handling and availability of the salt of the compound (1) and the raw material thereof are easy, at least one type selected from the group consisting of sodium, potassium, magnesium, and calcium is more preferable.

One type of the salt of the compound (1) may be used alone, or two or more types thereof may be used in combination.

The compound (2) is a so-called 6-O-higher acylascorbic acid-3-phosphoric acid ester (also referred to as an ascorbic acid-3-phosphoric acid-6-higher fatty acid).

In the general formula (2), $R^2$ is a linear or branched alkyl group having 6 to 20 carbon atoms.

Preferred alkyl groups as $R^2$ are the same as the preferred alkyl group as $R^1$.

In the ascorbic acid derivative composition of the present invention, $R^1$ and $R^2$ are the same or are different from each other. In view of easy preparation of formulations, $R^1$ and $R^2$ are preferably the same. In addition, when $R^1$ and $R^2$ are the same group, it is also preferable from the viewpoint that the solubility of the compounds (1) and (2) in the formulation becomes equal. In particular, from the viewpoint of raw material availability or the like, it is particularly preferred that each of $R^1$ and $R^2$ be a linear alkyl group having 15 carbon atoms.

The salt of the compound (2) is one obtained by neutralizing the compound (2) with a base, and is a compound formed from an anion derived from the compound (2) and a counter ion (cation derived from the base).

The anion derived from the compound (2) is usually a monovalent to tetravalent anion in which a hydrogen atom is dissociated from at least one of four hydroxyl groups in the compound (2) (two hydroxyl groups bonded to the phosphorus atom and the hydroxyl groups bonded to the carbon atoms at the 2-position and 5-position on the ascorbic acid, respectively).

The counter ion forming a salt with the anion is not particularly limited as long as it does not substantially inhibit the use of ascorbic acid derivatives, and examples thereof include the same counter ions listed in the description of the salt of the compound (1). Because of easy availability of the salt of the compound (2) and the raw material thereof, easy incorporation of the ascorbic acid derivative compositions into a formulation containing an aqueous medium, or the like, as the counter ion, at least one type of metal ion selected from the group consisting of alkali metal ions and alkaline earth metal ions is preferred. That is, the salt of the compound (2) is preferably a salt of at least one type of metal selected from the group consisting of alkali metals and alkaline earth metals. As the aforementioned metal, as described earlier, at least one type selected from the group consisting of sodium, potassium, magnesium, and calcium is more preferable.

One type of the salt of the compound (2) may be used alone, or two or more types thereof may be used in combination.

In the ascorbic acid derivative composition of the present invention, the ratio of the salt of the compound (2) with respect to the total amount of the salt of the compound (1) and the salt of the compound (2) is from 0.1 to 10% by mass, preferably from 1 to 10% by mass, and more preferably from 5 to 10% by mass.

When the ratio of the salt of the compound (2) is from 0.1 to 10% by mass, as compared with the case where the ratio of the salt of the compound (2) is less than 0.1% by mass or more than 10% by mass, stability of the ascorbic acid derivative composition improves and the solubility in an aqueous medium such as water or an alcohol also improves.

Although the reason why the above effects are obtained is not clear, as for the improvement of stability, it is thought that by making a predetermined amount of the salt of the compound (2) to coexist with the salt of the compound (1), the buffering action occurs due to the coexistence of two types of phosphoric acid compounds, and the pH in the solution can be maintained at a constant level. In addition, the improvement of solubility is thought to be caused by the reduction of crystallinity of the salt of the compound (1) due to the presence of the salt of the compound (2).

[Production Method of Ascorbic Acid Derivative Composition]

The ascorbic acid derivative composition of the present invention can be produced using known methods, and the production method is not particularly limited.

As an example of the method for producing the ascorbic acid derivative composition of the present invention, a production method comprising a step of mixing the salt of the compound (1) and the salt of the compound (2) can be mentioned.

For each of the salt of the compound (1) and the salt of the compound (2), a commercially available product may be used or those produced by a known production method may be used.

The salt of the compound (1) can be produced by adding a base to neutralize the compound (1). As with the above case, the salt of the compound (2) can be produced by adding a base to neutralize the compound (2).

For each of the compound (1) and the compound (2) used for the neutralization, a commercially available product may be used, or those produced by a known production method may be used.

The compound (1) can be produced, for example, by the method described later in section [I].

The compound (2) can be produced, for example, by the method described later in section [II].

As another example of the method for producing the ascorbic acid derivative composition of the present invention, a production method comprising a step of neutralizing the mixture of the compound (1) and the compound (2) can be mentioned.

The above mixture can be prepared by mixing the compound (1) and the compound (2). In this case, the above production method comprises a step of obtaining a mixture by mixing the compound (1) and the compound (2); and a step of neutralizing the mixture.

The above mixture can also be prepared by the methods of section [III] or [IV] which will be described later. The method of section [III] comprises a step of obtaining a mixture of the compound (1) and the compound (2) by isomerizing a portion of the compound (1) under an acidic condition; and a step of neutralizing the mixture. The method of section [IV] comprises a step of obtaining a mixture of the compound (3) (ascorbic acid-2-phosphoric acid ester) and the compound (5) (ascorbic acid-3-phosphoric acid ester) by isomerizing a portion of the compound (3); a step of obtaining a mixture of the compound (1) and the compound (2) by esterification of the mixture; and a step of neutralizing the mixture obtained by the esterification.

In the present invention, in particular, it is preferable to adjust the condition of isomerization at the time of preparing the mixture in the method of section [III] so that a mixture in which the ratio of the compound (2) with respect to the total amount of the compound (1) and the compound (2) is from 0.1 to 10% by mass is obtained. In this manner, it is possible to obtain the ascorbic acid derivative composition of the present invention by simply neutralizing the obtained mixture.

However, the present invention is not limited thereto. For example, it is possible to adjust by further adding the compound (1) or the compound (2) to the mixture obtained by the isomerization so that the ratio of the compound (2) with respect to the total amount of the compound (1) and the compound (2) is a predetermined ratio. In addition, it is also possible to isolate each of the compound (1) and compound (2) in the mixture and then to perform operations such as mixing again.

The neutralization of the mixture can be carried out by adding a base to the mixture, as in the case of neutralization of the compound (1) and the compound (2) described above.

[I] Production Method of Compound (1):

In this method, the compound (1) is produced by the following reaction. That is, the compound (1) is obtained by reacting a compound (3) represented by a formula (3) shown below with at least one type of compound (4) represented by a general formula (4) shown below.

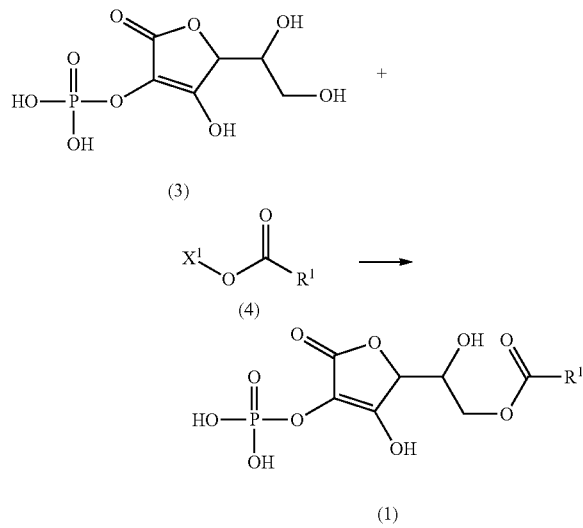

(In the formula, $R^1$ represents a linear or branched alkyl group of 6 to 20 carbon atoms, and $X^1$ represents a hydrogen atom, a cation, or an alkyl group of 1 to 5 carbon atoms.)

The compound (3) is an ascorbic acid-2-phosphoric acid ester. As the compound (3), those that are commercially available may be used, or those synthesized by a conventional method may be used.

The compound (4) is a fatty acid, an ester or salt thereof.

$R^1$ in the general formula (4) is the same as $R^1$ in the general formula (1).

$X^1$ is a hydrogen atom, a cation, or a linear or branched alkyl group of 1 to 5 carbon atoms. Examples of the cation include alkali metal ions and alkaline earth metal ions, and of these, sodium ions, potassium ions, magnesium ions, and calcium ions are preferred.

As $X^1$, a hydrogen atom, a methyl group, or an ethyl group is preferable, and a hydrogen atom is particularly preferable.

Examples of the compound (4) include, but not limited to, enanthic acid, caprylic acid, pelargonic acid, capric acid, lauric acid, myristic acid, palmitic acid, margaric acid, stearic acid, methyl enanthate, ethyl enanthate, propyl enanthate, butyl enanthate, methyl caprylate, ethyl caprylate, propyl caprylate, butyl caprylate, methyl pelargonate, ethyl pelargonate, propyl pelargonate, butyl pelargonate, methyl caprate, ethyl caprate, propyl caprate, butyl caprate, methyl laurate, ethyl laurate, propyl laurate, butyl laurate, methyl myristate, ethyl myristate, propyl myristate, butyl myristate, methyl palmitate, ethyl palmitate, propyl palmitate, butyl palmitate, methyl margarate, ethyl margarate, propyl margarate, butyl margarate, methyl stearate, ethyl stearate, propyl stearate, and butyl stearate. Among these, lauric acid, myristic acid, palmitic acid, stearic acid, methyl laurate, methyl myristate, methyl palmitate, methyl stearate, ethyl laurate, ethyl myristate, ethyl palmitate, ethyl stearate, or the like is preferred from the viewpoint of easy availability.

As the compound (4), those produced by a known production method may be used, or a commercially available product may be used.

One type of the compound (4) may be used alone or two or more types thereof may be used in combination.

The reaction of the compound (3) with the compound (4) is preferably carried out in the presence of a condensing agent and/or a dehydrating agent.

Although the condensing agent is not particularly limited, for example, N,N'-dicyclohexylcarbodiimide, N,N'-diisopropylcarbodiimide, N-ethyl-N'-3-dimethylaminopropylcarbodiimide, benzotriazol-1-yl-tris(dimethylamino)phosphonium hexafluorophosphide salts, diphenylphosphoryl azide or the like can be suitably used. Among these, the use of N,N'-diisopropylcarbodiimide is preferred.

Although the dehydrating agent is not particularly limited, for example, phosphorus pentoxide, solid phosphoric acid, titanium oxide, alumina, sulfuric acid or the like can be suitably used. Among these, it is preferable to use sulfuric acid (and more preferably a concentrated sulfuric acid of 95% by mass or more).

In the reaction of the compound (3) with the compound (4), it is preferable to carry out the reaction by using only a condensing agent and/or a dehydrating agent as a solvent and not to add any other solvents. Among these, the use of concentrated sulfuric acid as an only solvent is most preferred.

In the case of adding a solvent, for example, dioxane, dimethylformamide, dimethylacetamide, tetrahydrofuran, acetone, toluene, ethylbenzene, methyl-t-butyl ether or the like can be used.

The amount of the raw material (compound (3), compound (4)) used in the above reaction is preferably an equimolar amount. That is, it is preferable to react the compound (3) with the compound (4) in an equimolar amount with respect to the compound (3). However, the present invention is not limited thereto, and either one of the compound (3) and the compound (4) may be in excess, as long as this does not cause problems in isolation, purification, or the like.

The reaction time and reaction temperature can be set arbitrarily by taking into account the type of compound (4) (for example, the compound (4) being any one of a free fatty acid, an ester or a salt), and the amount used and type of the condensing agent and/or the dehydrating agent. The reaction time is preferably from 1 to 60 hours, and more preferably from 1 hour to 12 hours. The reaction temperature is preferably from 5° C. to 70° C., and more preferably from 15° C. to 50° C.

The amount of water brought into the reaction solution from the raw material and the condensing agent and/or dehydrating agent which is a catalyst is suitably not more than 10% by mass, and preferably not more than 5% by mass.

After the reaction, isolation and purification of the compound (1) may be carried out.

The isolation and purification method is not particularly limited, and general methods such as solvent extraction, washing, salting-out and column chromatography can be used. For example, the isolation and purification can be carried out by ether extraction or washing with a non-polar solvent such as hexane. If necessary, further purification can also be carried out by a method, such as reverse phase chromatography.

It is possible to obtain a salt of the compound (1) by adding a base to neutralize the compound (1). The base used for neutralization can be appropriately selected from among the bases known in the art in accordance with the type of the salt to be produced. Specific examples of the base include sodium hydroxide, potassium hydroxide, magnesium hydroxide, calcium hydroxide, barium hydroxide, ammonia, monoethanolamine, triethanolamine, dicyclohexylamine, metal alkoxides (such as sodium methoxide, potassium methoxide, sodium ethoxide, and potassium-t-butoxide), and metal oxides (such as magnesium oxide and calcium oxide). Among these, metal alkoxides, sodium hydroxide, potassium hydroxide, magnesium hydroxide, calcium hydroxide, magnesium oxide, calcium oxide, and the like are preferred.

During the neutralization reaction, water, alcohols such as methanol and ethanol, and the like can be used as a solvent. It is preferable to add the compound (1) so that the concentration of the compound (1) is a ratio of about 1 to 30% by mass, relative to the solvent, and then to carry out the reaction by adding a base thereto.

The pH at the time of reaction is preferably about 5 to 9.

The salt formed and precipitated by the reaction can be collected and purified, for example, by a conventional method such as filtration and solvent washing.

[II] Production Method of Compound (2):

In this method, the compound (2) is produced by the following reaction. That is, the compound (2) is obtained by reacting a compound (5) represented by a formula (5) shown below with at least one type of compound (6) represented by a general formula (6) shown below.

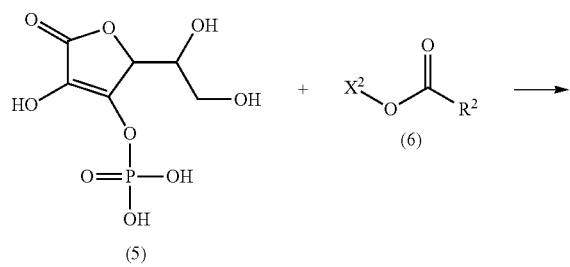

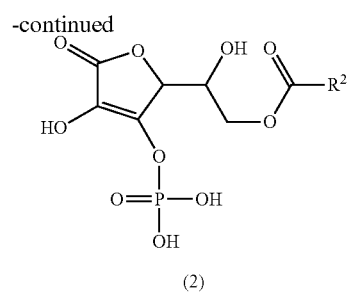

(In the formula, $R^2$ represents a linear or branched alkyl group of 6 to 20 carbon atoms, and $X^2$ represents a hydrogen atom, a cation, or an alkyl group of 1 to 5 carbon atoms.)

The compound (5) is an ascorbic acid-3-phosphoric acid ester. As the compound (5), those that are commercially available may be used, or those synthesized by a conventional method may be used. As an example of the synthesis method, a method described in Japanese Examined Patent Application, Second Publication No. Sho 43-9218 for producing an ascorbic acid-3-phosphoric acid ester by reacting ascorbic acid with phosphorus oxychloride in the presence of a tertiary amine and using ketones as the solvent, and the like can be cited.

The compound (6) is a fatty acid, an ester or salt thereof. $R^2$ in the general formula (6) is the same as $R^2$ in the general formula (2). $R^2$ may be the same as or different from $R^1$.

As examples of $X^2$, the same as those described above for $X^1$ in the general formula (4) can be cited.

As examples of the compound (6), the same as those described above for the compound (4) can be cited.

One type of the compound (6) may be used alone or two or more types thereof may be used in combination.

The reaction of the compound (5) with the compound (6) can be carried out in the same manner as in the reaction of the compound (3) with the compound (4). For example, the condensing agent and/or dehydrating agent to be used, the solvent, the amount of raw materials used, the reaction temperature, the reaction time, the water content which is brought into the reaction solution from the raw material and the catalyst, and the isolation and purification method are also the same.

By adding a base to the obtained compound (2) for neutralization, a salt of the compound (2) is obtained. The neutralization can be carried out in a similar manner to the method described above in section [I].

[III] the Method of Producing a Mixture of the Compound (1) and the Compound (2) by Isomerization—Option 1:

In this method, a portion of the compound (1) is isomerized under an acidic condition to produce the compound (2), thereby obtaining a mixture of the compound (1) and the compound (2).

More specifically, the compound (1) is dissolved in water or water containing an alcohol, and the pH of the obtained solution is controlled under an acidic condition. As a result, as shown in the following reaction formula, a phosphoryl group of the compound (1) is transferred to form the compound (2).

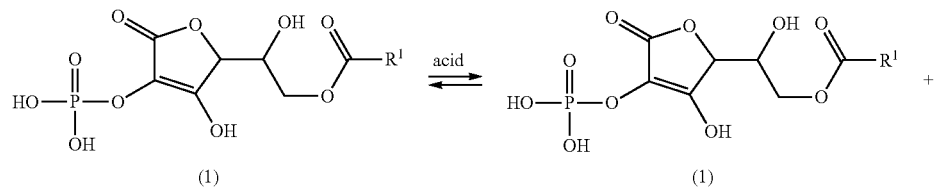

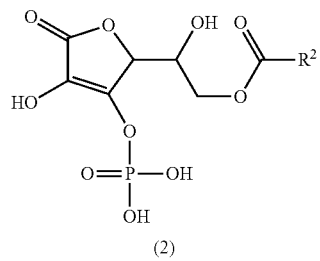

(2)

(In the formula, $R^1$ is the same as $R^1$ defined in the formula (1) and $R^2$ is the same as $R^2$ defined in the formula (1).)

As the alcohol, the same alcohols as those described later in an aqueous medium can be cited.

The "acidic condition" in the above reaction is preferably a pH of 1 to 6, and more preferably a pH of 2 to 4. If the pH is higher than 6, the reaction takes too much time and thus inefficient, and if the pH is lower than 1, decomposition of the compound (1) and compound (2) occurs easily.

It should be noted that in the present description and claims, the pH value is a value at 25° C.

The pH can be controlled by the addition of an acid. The acid used for the control of pH is not particularly limited. Specific examples of the acid include inorganic acids such as sulfuric acid, nitric acid, and hydrochloric acid, and organic acids such as methanesulfonic acid and trifluoroacetic acid. Among these, hydrochloric acid is preferred.

The reaction temperature is preferably from 10 to 55° C., and more preferably from 20 to 30° C.

The reaction time varies depending on the pH and the temperature, but is preferably between 1 to 24 hours. When the reaction time is too long, it is possible that the ratio of the compound (2) becomes excessive.

By stopping the isomerization reaction at the appropriate time point, it is possible to obtain a composition containing the compounds (1) and (2) at a predetermined ratio. The appropriate time point for stopping the isomerization reaction can be confirmed by, for example, monitoring the composition of the reaction system through a known method.

As a method of stopping the isomerization reaction, a method of removing the acid by neutralization with a base and solvent extraction can be cited.

After the completion of the reaction, purification of the mixture of the compound (1) and the compound (2) may be further carried out.

By adding a base to, and thereby neutralizing, the obtained mixture of the compound (1) and the compound (2), a mixture of the salt of the compound (1) and the salt of the compound (2) is obtained. The neutralization can be carried out in the same manner as in the method described above in section [I].

[IV] the Method of Producing a Mixture of the Compound (1) and the Compound (2) by Isomerization—Option 2:

In this method, first, as shown in the following reaction formula, a portion of the compound (3) is isomerized under an acidic condition to produce the compound (5), thereby obtaining a mixture of the compound (3) and the compound (5).

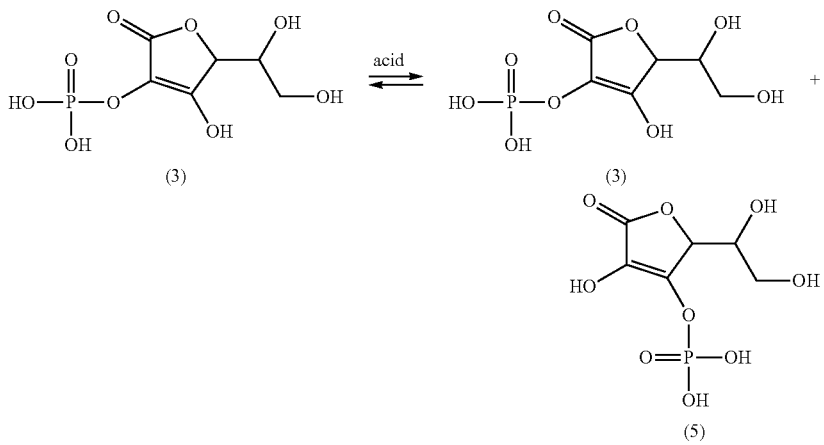

The "acidic condition" in the method of section [IV] is, as in the method of section [III], preferably a pH of 1 to 6, and more preferably a pH of 2 to 4.

The method for setting an acidic condition inside the system in the above reaction is not particularly limited, and, for example, a method of adding an acid can be mentioned. As the acid to be used, any of the known acids may be used, and examples thereof include hydrochloric acid, sulfuric acid, sulfonic acids, nitric acid, boric acid, and carboxylic acids such as acetic acid, citric acid, formic acid, oxalic acid, tartaric acid, and lactic acid. Among these, acetic acid, sulfuric acid, and hydrochloric acid are preferred, and sulfuric acid or concentrated sulfuric acid is the most preferred.

At the time of the above reaction, a solvent may be used, although it is preferable not to use a solvent. Specific examples of the solvent include dioxane, dimethylformamide, dimethylacetamide, tetrahydrofuran, acetone, toluene, ethylbenzene, and methyl-t-butyl ether.

The isomerization reaction may be carried out by the same method as in the isomerization reaction from the compound (1) to the mixture of the compounds (1) and (2), as described above in section [III].

Next, the mixture obtained by the above isomerization reaction (a mixture of the compound (3) and the compound (5)) is reacted with a compound (4) (esterification). As a result, a mixture of the compound (1) and the compound (2) is obtained.

The esterification can be carried out in the same manner as in the reaction of the compound (3) with the compound (4), as described above in section [I].

By adding a base to, and thereby neutralizing, the obtained mixture of the compound (1) and the compound (2), a mixture of the salt of the compound (1) and the salt of the compound (2) is obtained. The neutralization can be carried out in the same manner as in the method described above in section [I].

The ascorbic acid derivative composition of the present invention exhibits excellent stability and also excellent solubility in an aqueous medium by including the salt of the compound (1) and the salt of the compound (2) at a specific mass ratio.

For this reason, it is possible to dissolve the ascorbic acid derivative composition of the present invention in at least one type of aqueous medium selected from the group consisting of water and an alcohol to produce an ascorbic acid derivative solution. In addition, the ascorbic acid derivative solution obtained in this manner is one in which the content of the ascorbic acid derivative is hardly reduced during storage.

The alcohol in an aqueous medium may by any one as long as it is miscible uniformly with water, and examples thereof include lower monoalcohols such as ethanol, methanol, isopropyl alcohol, 1-butanol, 2-butanol, and benzyl alcohol; higher alcohols such as isostearyl alcohol, octyl dodecanol, hexyl decanol, cholesterol, phytosterol, lauryl alcohol, myristyl alcohol, cetanol, stearyl alcohol, oleyl alcohol, behenyl alcohol, and cetostearyl alcohol; and polyhydric alcohols such as ethylene glycol, diethylene glycol, triethylene glycol, polyethylene glycol, propylene glycol, dipropylene glycol, polypropylene glycol, glycerol, diglycerol, polyglycerol, 3-methyl-1,3-butanediol, 1,3-butanediol, 1,2-pentanediol, and 1,2-hexanediol. Among these, ethanol, 1,3-butanediol, and glycerol are preferred.

As the aqueous medium, water or water containing an alcohol is preferred.

The content of the ascorbic acid derivative in the ascorbic acid derivative solution is preferably from 0.01 to 20% by mass, and more preferably from 0.5 to 10% by mass, with respect to the total mass of the ascorbic acid derivative solution.

Because the above effects can be achieved, the ascorbic acid derivative composition of the present invention and the ascorbic acid derivative solution obtained by dissolving this in an aqueous medium are useful as raw materials of medicines, agricultural chemicals, animal drugs, foods, feeds, cosmetics, and the like, and are particularly useful as raw materials of the skin external preparations.

For example, a skin external preparation can be prepared by further adding the components usually used in the skin external preparations to the ascorbic acid derivative composition of the present invention or the ascorbic acid derivative solution.

Examples of the skin external preparations include cosmetics and medicines, and cosmetics are preferred.

The content of the ascorbic acid derivative composition of the present invention (total amount of the salt of the compound (1) and the salt of the compound (2)) in the skin external preparation is not particularly limited, but is preferably from 0.1 to 10% by mass, and more preferably from 0.5 to 5% by mass, with respect to the total amount of the skin external preparation.

As the components usually used in the skin external preparations, for example, hydrocarbons, natural fats, fatty acids, higher alcohols, alkyl glyceryl ethers, esters, silicone oils, polyhydric alcohols, monovalent lower alcohols, sugars, polymers, anionic surfactants, cationic surfactants, amphoteric surfactants, nonionic surfactants, natural surfactants, ultraviolet absorbers, powders, coloring materials, amino acids, peptides, vitamins, vitamin-like acting factors, preservatives, antioxidants, sequestering agents, moisturizers, anti-inflammatory agents, pH adjusting agents, salts, organic acids, skin whitening agents, essential oils, terpenes, fragrances, water and the like can be mentioned.

When the skin external preparation is a cosmetic, it is also possible to further add an existing cosmetic ingredient at a typical concentration. For example, it is possible to use all of the cosmetic ingredients listed in The Japanese Standards of Cosmetic Ingredients $2^{nd}$ Edition, Annotation (edited by Society of Japanese Pharmacopoeia and published by Yakuji Nippo, Ltd. (1984)), The Japanese Cosmetic Ingredients Codex (supervised by Ministry of Health and Welfare, Pharmaceutical Affairs Bureau, Examination Division and published by Yakuji Nippo, Ltd. (1993)), Supplement to The Japanese Cosmetic Ingredients Codex (supervised by Ministry of Health and Welfare, Pharmaceutical Affairs Bureau, Examination Division and published by Yakuji Nippo, Ltd. (1993)), The Comprehensive Licensing Standards Of Cosmetics by Category (supervised by Ministry of Health and Welfare, Pharmaceutical Affairs Bureau, Examination Division and published by Yakuji Nippo, Ltd. (1993)), The Japanese Cosmetic Ingredients Codex by Category (supervised by Ministry of Health and Welfare, Pharmaceutical Affairs Bureau, Examination Division and published by Yakuji Nippo, Ltd. (1997)), and Dictionary of Cosmetic Ingredients (Nikko Chemicals Co., Ltd. (1991)), and the like.

The form of the skin external preparation is not particularly limited as long as it is one that is used by being brought into contact with the skin at the time of use, and can be appropriately set in accordance with the application. For example, it is possible to apply to a lotion, emulsion, cream, pack or the like. As the form of the skin external preparation, in view of the usefulness of the present invention, the form including an aqueous medium as described earlier is preferred.

The formulation of the ascorbic acid derivative composition or ascorbic acid derivative solution into a skin external preparation or the like can be carried out by a conventional method in accordance with the form.

EXAMPLES

The present invention will be described below in further detail using Examples. However, the present invention is in no way limited by these Examples.

The measurement was conducted by high performance liquid chromatography (HPLC) under the measurement conditions shown below, and the yield of the compounds synthesized in Production Example to be described later was calculated from the results thereof.

(Measurement Conditions for High Performance Liquid Chromatography in the Evaluation of Yield)

Two columns: Shodex OHpak SB802.5 HQ (manufactured by Showa Denko K.K.);

Temperature: 40° C.;
Eluent: aqueous solution of sodium sulfate and phosphoric acid (0.03 M $Na_2SO_4$+0.03 M $H_3PO_4$)/tetrahydrofuran=½ (volume ratio);
Flow rate: 0.5 mL/min;
Injection volume: 20 μL;
Detection: UV detector, wavelength 270 nm.

Production Example 1

L-ascorbic acid-2-phosphoric acid-6-palmitate 10 mmol (3.8 g) of a magnesium salt of L-ascorbic acid-2-phosphate (manufactured by Showa Denko K.K.) was dissolved in 60 mL of concentrated sulfuric acid at room temperature and to the resulting solution, 15 mmol (3.8 g) of palmitic acid was added, and the thus obtained mixture was homogeneously stirred. After standing at room temperature for 24 hours, the reaction mixture was poured into about 300 mL of ice water, and the precipitate was extracted twice with 200 mL of diethyl ether. The extracts were combined and washed with 300 mL of 2N hydrochloric acid containing 30% isopropanol, and the diethyl ether was removed by distillation under reduced pressure. The deposit was washed twice with about 200 mL of n-hexane and then dried under reduced pressure to obtain 3.2 g of L-ascorbic acid-2-phosphoric acid-6-palmitate (yield: 65%).

Production Example 2

Sodium Salt of L-ascorbic acid-2-phosphoric acid-6-palmitate

The L-ascorbic acid-2-phosphoric acid-6-palmitate obtained in Production Example 1 was added to methanol so that the concentration thereof became 5% by mass, and sodium methoxide was gradually added thereto with stirring until the pH became about 8 to precipitate a crystal. The resulting crystals were collected by filtration, and then washed twice with the same amount of methanol as was used in the first dissolution and dried under reduced pressure to obtain a sodium salt of L-ascorbic acid-2-phosphoric acid-6-palmitate.

Production Example 3

L-ascorbic acid-3-phosphoric acid-6-palmitate

The same operation as in Production Example 1 was carried out with the exception that a magnesium salt of L-ascorbic acid-3-phosphate was used in place of a magnesium salt of L-ascorbic acid-2-phosphate, thereby obtaining 3.0 g of L-ascorbic acid-3-phosphoric acid-6-palmitate (yield: 61%).

Production Example 4

Sodium Salt of L-ascorbic acid-3-phosphoric acid-6-palmitate

The same operation as in Production Example 2 was carried out with the exception that the L-ascorbic acid-3-phosphoric acid-6-palmitate obtained in Production Example 3 was used in place of L-ascorbic acid-2-phosphoric acid-6-palmitate, thereby obtaining a sodium salt of L-ascorbic acid-3-phosphoric acid-6-palmitate.

Production Example 5

Isomerization of 2-phosphate Form to 3-phosphate Form 2.0 g of the L-ascorbic acid-2-phosphoric acid-6-palmitate obtained in Production Example 1 was dissolved in 100 mL of methanol, and was adjusted to a pH of 2 with 36% hydrochloric acid. The resulting solution was stirred for 5 hours at 30° C., and methanol was removed by distillation under reduced pressure. The deposit was washed twice with about 150 mL of n-hexane and then dried under reduced pressure to obtain 2.0 g of a mixture of L-ascorbic acid-2-phosphoric acid-6-palmitate and L-ascorbic acid-3-phosphoric acid-6-palmitate (yield: 100%).

Production Example 6

Sodium Salt of a Mixture of L-ascorbic acid-2-phosphoric acid-6-palmitate and L-ascorbic acid-3-phosphoric acid-6-palmitate The same operation as in Production Example 2 was carried out with the exception that the mixture obtained in Production Example 5 was used in place of L-ascorbic acid-2-phosphoric acid-6-palmitate, thereby obtaining a mixture of a sodium salt of L-ascorbic acid-2-phosphoric acid-6-palmitate and a sodium salt of L-ascorbic acid-3-phosphoric acid-6-palmitate.

The composition ratio of the mixture was (sodium salt of L-ascorbic acid-2-phosphoric acid-6-palmitate):(sodium salt of L-ascorbic acid-3-phosphoric acid-6-palmitate)=97.7:2.3 (mass ratio).

Test Example 1

Storage Stability Test

The sodium salt of L-ascorbic acid-2-phosphoric acid-6-palmitate obtained in Production Example 2 and the sodium salt of L-ascorbic acid-3-phosphoric acid-6-palmitate obtained in Production Example 4 were mixed at a ratio (% by mass) shown in Table 1 to prepare ascorbic acid derivative compositions of Examples 1 to 3.

The mixture obtained in Production Example 6 ((sodium salt of L-ascorbic acid-2-phosphoric acid-6-palmitate): (sodium salt of L-ascorbic acid-3-phosphoric acid-6-palmitate)= 97.7:2.3 (mass ratio)) was used as it is as an ascorbic acid derivative composition of Example 4.

The sodium salt of L-ascorbic acid-2-phosphoric acid-6-palmitate obtained in Production Example 2 was used as it is as an ascorbic acid derivative of Comparative Example 1, and the sodium salt of L-ascorbic acid-3-phosphoric acid-6-palmitate obtained in Production Example 4 was used as it is as an ascorbic acid derivative of Comparative Example 2.

The obtained ascorbic acid derivative composition or ascorbic acid derivative was dissolved in purified water so that the concentration of ascorbic acid derivative was 2% by mass. The resulting solution was placed in a glass bottle with a lid and was left to stand for 10 days at 40° C. (light shielding condition).

The concentration of ascorbic acid derivative in each of the solutions obtained before standing (immediately after preparation) and after standing for 10 days was measured, and the "residual ratio" was determined from the results by the following formula.

The concentration of ascorbic acid derivative contained in the solution was measured by the same measuring conditions as in the evaluation of the yield, with a high performance liquid chromatography apparatus using the Shodex SB 802.5 HQ column (manufactured by Showa Denko K.K.).

Note that in Examples 1 to 4 and in Comparative Examples 1 to 2, as the concentration of the ascorbic acid derivative, the total concentration (% by mass) of the sodium salt of L-ascorbic acid-2-phosphoric acid-6-palmitate and the sodium salt of L-ascorbic acid-3-phosphoric acid-6-palmitate was determined.

Residual ratio(%)=100×[concentration of ascorbic acid derivative in the solution after standing(% by mass)]/[concentration of ascorbic acid derivative in the solution before standing(% by mass)].

combination of a sodium salt of L-ascorbic acid-2-phosphoric acid-6-palmitate and a sodium salt of L-ascorbic acid-3-phosphoric acid-6-palmitate.

Test Example 2

Solubility Test

Each substance shown in Table 2 was prepared at the ratio (% by mass) indicated in Table 2 so that the total amount was 100 g. First, pure water or a mixture of pure water and methanol serving as a solvent was placed in a beaker having a

TABLE 1

|  | Ex. 1 | Ex. 2 | Ex. 3 | Ex. 4 | Comp. Ex. 1 | Comp. Ex. 2 |
| --- | --- | --- | --- | --- | --- | --- |
| Sodium salt of L-ascorbic acid-2-phosphoric acid-6-palmitate of Production Example 2 | 95% by mass | 99% by mass | 99.5% by mass | — | 100% by mass | — |
| Sodium salt of L-ascorbic acid-3-phosphoric acid-6-palmitate of Production Example 4 | 5% by mass | 1% by mass | 0.5% by mass | — | — | 100% by mass |
| Mixture of sodium salt of L-ascorbic acid-2-phosphoric acid-6-palmitate and sodium salt of L-ascorbic acid-3-phosphoric acid-6-palmitate of Production Example 6 | — | — | — | 100% by mass | — | — |
| Residual ratio (%) | 96.1 | 94.4 | 93.2 | 94.8 | 88.6 | 83.9 |

As shown in the above results, Examples 1 to 4 in which the ascorbic acid derivative was a mixture of a sodium salt of L-ascorbic acid-2-phosphoric acid-6-palmitate and a sodium salt of L-ascorbic acid-3-phosphoric acid-6-palmitate exhibited higher residual ratio than that of Comparative Example 1 in which the ascorbic acid derivative was composed only of a sodium salt of L-ascorbic acid-2-phosphoric acid-6-palmitate and that of Comparative Example 2 in which the ascorbic acid derivative was composed only of a sodium salt of L-ascorbic acid-3-phosphoric acid-6-palmitate. From the results, it was possible to confirm that that the storage stability in an aqueous medium solution was improved by using a capacity of 200 mL, and the beaker was immersed in a water bath which was controlled to 20° C. Then, stirring was performed at a rotational speed of 500 rpm with a stirrer chip having a diameter of 2.5 cm, and the ascorbic acid derivative was mixed at the point where the liquid temperature reached 20° C. This time point was set as the zero point and the time (min) until the solid became absent in the mixture was measured. As for the end point, visual observation was carried out every 5 minutes from the start of the stirring, and the time point at which the mixture became clear was determined as the end point.

TABLE 2

|  | Ex. 5 | Ex. 6 | Ex. 7 | Ex. 8 | Ex. 9 | Ex. 10 | Comp. Ex. 3 | Comp. Ex. 4 |
| --- | --- | --- | --- | --- | --- | --- | --- | --- |
| Sodium salt of L-ascorbic acid-2-phosphoric acid-6- palmitate of Production Example 2 | 9.5% by mass | 9.9% by mass | 9.95% by mass | — | 9.5% by mass | 9.9% by mass | 10% by mass | 10% by mass |
| Sodium salt of L-ascorbic acid-3-phosphoric acid-6-palmitate of Production Example 4 | 0.5% by mass | 0.1% by mass | 0.05% by mass | — | 0.5% by mass | 0.1% by mass | — | — |
| Mixture of sodium salt of L-ascorbic acid-2-phosphoric acid-6-palmitate and sodium salt of L-ascorbic acid-3-phosphoric acid-6-palmitate of Production Example 6 | — | — | — | 10% by mass | — | — | — | — |
| Pure water | 90% by mass | 90% by mass | 90% by mass | 90% by mass | 70% by mass | 70% by mass | 90% by mass | 70% by mass |
| Methanol | — | — | — | — | 20% by mass | 20% by mass | — | 20% by mass |
| Time required for dissolution | 20 min | 20 min | 25 min | 20 min | 30 min | 35 min | 50 min | 65 min |

As shown in the above results, in Examples 5 to 10 in which the ascorbic acid derivative was a mixture of a sodium salt of L-ascorbic acid-2-phosphoric acid-6-palmitate and a sodium salt of L-ascorbic acid-3-phosphoric acid-6-palmitate, as compared with Comparative Examples 3 to 4 in which the ascorbic acid derivative was composed only of a sodium salt of L-ascorbic acid-2-phosphoric acid-6-palmitate, the ascorbic acid derivative was dissolved in water or water containing an alcohol in a short period of time. From the results, it was possible to confirm that that the solubility in an aqueous medium was improved by using a combination of a sodium salt of L-ascorbic acid-2-phosphoric acid-6-palmitate and a sodium salt of L-ascorbic acid-3-phosphoric acid-6-palmitate.

Test Example 3

Storage Stability Test (Emulsion Cream)

Emulsion creams having compositions (unit: % by mass) shown in Table 3 were prepared by the following procedure.

First, a phase I (oil phase) was prepared by mixing and dissolving each of the materials shown in column I of Table 3 at 80° C. at a composition ratio indicated in Table 3. The phase I was kept at 80° C.

Separately, a phase II (aqueous phase) was prepared by mixing and dissolving each of the materials shown in column II of Table 3 at 80° C. at a composition ratio indicated in Table 3. The phase II was kept at 80° C.

The phase II was added to the phase I, and the mixture was emulsified by cooling while stirring, and was then cooled to 30° C. to prepare an O/W type emulsion cream.

The resulting emulsion cream was placed in a glass bottle with a lid and was allowed to stand for one month at 40° C. (light shielding condition).

The concentration of ascorbic acid derivative in each of the emulsion creams obtained before standing (immediately after preparation) and after standing for one month was measured, and the "residual ratio" was determined from the results by the following formula.

The method of measuring the concentration of ascorbic acid derivative was the same as in Test Example 1.

Note that as the concentration of the ascorbic acid derivative, in Examples 11 to 12 and in Comparative Examples 5 and 7 to 8, the total concentration (% by mass) of the sodium salt of L-ascorbic acid-2-phosphoric acid-6-palmitate and the sodium salt of L-ascorbic acid-3-phosphoric acid-6-palmitate was determined, and in Examples 13 to 14 and in Comparative Example 6, the total concentration (% by mass) of an ammonium salt of L-ascorbic acid-2-phosphoric acid-6-arachidate and a barium salt of L-ascorbic acid-3-phosphoric acid-6-caprate was determined.

Residual ratio(%)=100×[concentration of ascorbic acid derivative in the emulsion cream after standing(% by mass)]/[concentration of ascorbic acid derivative in the emulsion cream before standing(% by mass)].

TABLE 3

|   |   | Ex. 11 | Ex. 12 | Ex. 13 | Ex. 14 | Comp. Ex. 5 | Comp. Ex. 6 | Comp. Ex. 7 | Comp. Ex. 8 |
|---|---|---|---|---|---|---|---|---|---|
| I | Hydrogenated rapeseed oil alcohol | 4.20 | 4.20 | 4.20 | 4.20 | 4.20 | 4.20 | 4.20 | 4.20 |
|   | Isononyl isononanoate | 6.00 | 6.00 | 6.00 | 6.00 | 6.00 | 6.00 | 6.00 | 6.00 |
|   | Squalane | 9.60 | 9.60 | 9.60 | 9.60 | 9.60 | 9.60 | 9.60 | 9.60 |
|   | Octyldodecyl myristate | 4.80 | 4.80 | 4.80 | 4.80 | 4.80 | 4.80 | 4.80 | 4.80 |
|   | POE (20) sorbitan stearate | 1.00 | 1.00 | 1.00 | 1.00 | 1.00 | 1.00 | 1.00 | 1.00 |
|   | Tocopherol | 0.20 | 0.20 | 0.20 | 0.20 | 0.20 | 0.20 | 0.20 | 0.20 |
|   | Propylparaben | 0.05 | 0.05 | 0.05 | 0.05 | 0.05 | 0.05 | 0.05 | 0.05 |
|   | Xanthan gum | 0.10 | 0.10 | 0.10 | 0.10 | 0.10 | 0.10 | 0.10 | 0.10 |
| II | 1,3-butylene glycol | 4.80 | 4.80 | 4.80 | 4.80 | 4.80 | 4.80 | 4.80 | 4.80 |
|   | Glycerol | 4.80 | 4.80 | 4.80 | 4.80 | 4.80 | 4.80 | 4.80 | 4.80 |
|   | Citric acid 3 Na | 0.40 | 0.40 | 0.40 | 0.40 | 0.40 | 0.40 | 0.40 | 0.40 |
|   | Sodium salt of L-ascorbic acid-2-phosphoric acid-6-palmitate | 0.90 | 0.95 |   |   | 1.00 |   |   | 0.80 |
|   | Sodium salt of L-ascorbic acid-3-phosphoric acid-6-palmitate | 0.10 | 0.05 |   |   |   |   | 1.00 | 0.20 |
|   | Ammonium salt of L-ascorbic acid-2-phosphoric acid-6-arachidate |   |   | 0.90 | 0.95 |   | 1.00 |   |   |
|   | Barium salt of L-ascorbic acid-3-phosphoric acid-6-caprate |   |   | 0.10 | 0.05 |   |   |   |   |
|   | Purified water | 63.05 | 63.05 | 63.05 | 63.05 | 63.05 | 63.05 | 63.05 | 63.05 |
|   | Residual ratio % | 98 | 98 | 90 | 90 | 76 | 72 | 73 | 82 |

For the ascorbic acid derivatives as shown in Table 3, the following were used, respectively.

Sodium salt of L-ascorbic acid-2-phosphoric acid-6-palmitate: one obtained in Production Example 2.

Sodium salt of L-ascorbic acid-3-phosphoric acid-6-palmitate: one obtained in Production Example 4.

Ammonium salt of L-ascorbic acid-2-phosphoric acid-6-arachidate: one obtained by the same production method as in Production Examples 1 and 2 with the exception that palmitic acid was changed to arachidic acid, and sodium hydroxide was changed to ammonia (aqueous ammonia).

Barium salt of L-ascorbic acid-3-phosphoric acid-6-caprate: one obtained by the same production method as in Production Examples 3 and 4 with the exception that palmitic acid was changed to capric acid, and sodium hydroxide was changed to barium hydroxide.

It should be noted that the POE (20) sorbitan stearate in Table 3 shows a polyoxyethylene sorbitan stearate having an average addition mole number of oxyethylene groups of 20.

As shown in the above results, Examples 11 to 14 in which the ascorbic acid derivative was a mixture of a salt of L-ascorbic acid-2-phosphoric acid-6-higher fatty acid and a salt of L-ascorbic acid-3-phosphoric acid-6-higher fatty acid exhibited a high residual ratio of 90% or more.

On the other hand, Comparative Examples 5 to 6 in which the ascorbic acid derivative was composed only of a salt of L-ascorbic acid-2-phosphoric acid-6-higher fatty acid and Comparative Example 7 in which the ascorbic acid derivative was composed only of a salt of L-ascorbic acid-3-phosphoric acid-6-higher fatty acid exhibited a lower residual ratio, as compared with Examples 11 to 14.

Even when the ascorbic acid derivative was a mixture of a salt of L-ascorbic acid-2-phosphoric acid-6-higher fatty acid and a salt of L-ascorbic acid-3-phosphoric acid-6-higher fatty acid, the residual ratio of Comparative Example 8 in which the ratio of the salt of L-ascorbic acid-3-phosphoric acid-6-higher fatty acid with respect to the total amount thereof was 20% by mass was improved over Comparative Examples 5 to 7, but was lower than that of Examples 11 to 14.

From the results, it was possible to confirm that that the storage stability in the emulsion cream was improved by using a combination of a salt of L-ascorbic acid-2-phosphoric acid-6-higher fatty acid and a small amount of a salt of L-ascorbic acid-3-phosphoric acid-6-higher fatty acid.

The invention claimed is:

1. A composition consisting of:
   a salt of a compound (1) represented by formula (1) shown below; and
   a salt of a compound (2) represented by formula (2) shown below,
   wherein a ratio of said salt of the compound (2) with respect to a total amount of said salt of the compound (1) and said salt of the compound (2) is from 0.1 to 10% by mass,

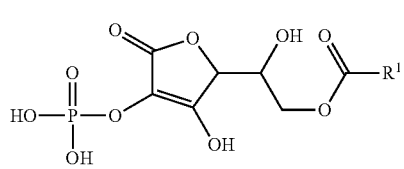
(1)

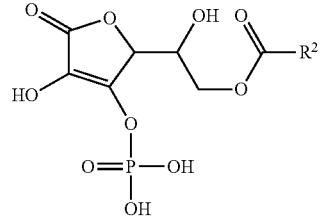
(2)

wherein $R^1$ represents a linear or branched alkyl group of 6 to 20 carbon atoms, $R^2$ represents a linear or branched alkyl group of 6 to 20 carbon atoms, and $R^1$ and $R^2$ are the same or are different from each other.

2. The composition according to claim 1, wherein $R^1$ in said formula (1) and $R^2$ in said formula (2) are the same.

3. The composition according to claim 1,
   wherein each of $R^1$ in said formula (1) and $R^2$ in said formula (2) is a linear alkyl group of 15 carbon atoms.

4. The composition according to claim 1,
   wherein each of said salt of the compound (1) and said salt of the compound (2) is a salt of at least one type of metal selected from the group consisting of an alkali metal and an alkaline earth metal.

5. The composition according to claim 1,
   wherein each of said salt of the compound (1) and said salt of the compound (2) is a salt of at least one type of metal selected from the group consisting of sodium, potassium, magnesium, and calcium.

6. A solution, which is obtained by dissolving the composition according to claim 1 in at least one type of aqueous medium selected from the group consisting of water and an alcohol.

7. A skin external preparation, which comprises the composition according to claim 1.

8. The skin external preparation according to claim 7, wherein the skin external preparation is a cosmetic.

9. A production method of the composition according to claim 1, wherein
   the method comprises a step of mixing said salt of the compound (1) and said salt of the compound (2).

10. A production method of the composition according to claim 1, wherein
    the method comprises:
    a step of obtaining a mixture of said compound (1) and said compound (2) by isomerizing a portion of said compound (1) under an acidic condition; and
    a step of neutralizing said mixture.

11. The production method according to claim 10, wherein said acidic condition is a pH of 1 to 6.

12. The skin external preparation according to claim 7, wherein the skin external preparation comprises at least one type of aqueous medium selected from the group consisting of water and an alcohol, and said composition has been dissolved in the aqueous medium.

13. The composition according to claim 1, wherein the ratio of the salt of the compound (2) is from 1 to 10% by mass.

14. The composition according to claim 1, wherein each of $R^1$ in said formula (1) and $R^2$ in said formula (2) is a linear or branched alkyl group of 12 to 16 carbon atoms.

15. The production method according to claim 11, wherein said acidic condition is a pH of 2 to 4.

16. The composition according to claim 1, wherein the ratio of the salt of the compound (2) with respect to the total amount of the salt of the compound (1) and the salt of the compound (2) is from 5 to 10% by mass.

* * * * *